United States Patent [19]
Arias-Alvarez

[11] Patent Number: 4,462,988
[45] Date of Patent: Jul. 31, 1984

[54] TREATMENT OF ARTHRITIS WITH BISULFITE
[75] Inventor: Jose A. Arias-Alvarez, Carpatos, Mexico
[73] Assignee: T&R Chemicals, Inc., Clint, Tex.
[21] Appl. No.: 498,489
[22] Filed: May 26, 1983
[51] Int. Cl.³ .............................................. A61K 33/04
[52] U.S. Cl. .................................................... 424/162
[58] Field of Search ......................................... 424/162

[56] References Cited
U.S. PATENT DOCUMENTS
4,327,083  4/1982  Alvarez ................................. 424/162

Primary Examiner—Stanley J. Friedman
Attorney, Agent, or Firm—Cushman, Darby & Cushman

[57] ABSTRACT
The treatment of arthritis with sulfites and bisulfites.

4 Claims, No Drawings

TREATMENT OF ARTHRITIS WITH BISULFITE

BACKGROUND OF THE INVENTION

Sodium bisulfite (usually shown by formula to be $NaHSO_3$) has heretofore been used for many commercial purposes, such as a preservative for prevention of the deterioration of liquids, such as food stuffs and pharmaceutical solids and solutions, and has been used medically externally for parasitic skin diseases and internally as a gastrointestinal antiseptic.

The sodium bisulfite of commerce consists chiefly of sodium metabisulfite, $Na_2S_2O_5$, and for purposes of this invention such is believed to possess the same properties as (and to be equivalent to) the true sodium bisulfite when dissolved in an aqueous solution.

The use of sodium bisulfite and metabisulfite in the treatment of hypertension is described in my U.S. Pat. No. 4,327,083 and is also described as an antithrombotic agent useful for prolonging both prothrombin time (PT) and partial thromboplastin time (PTT) of blood or blood plasma in my copending application Ser. No. 281,951 filed July 9, 1981, now U.S. Pat. No. 4,401,654.

BRIEF SUMMARY OF THE INVENTION

It has now been discovered that sodium bisulfite is useful in low doses and over extended periods in the treatment of the symptoms of arthritis and arthritic conditions when administered to humans in an aqueous dilute solution.

The method of the present invention is directed to the treatment of arthritis and symptoms experienced by those afflicted with arthritic conditions. The most common form of arthritis is rheumatoid arthritis which is characterized by a chronic inflammatory condition affecting particularly the small joints of the hands and feet, although the larger joints may be affected later. The synovial membrane typically swells forming pulpy masses or fringes causing the joints to be enlarged. A gradual destruction of the articular cartilage finally results in complete disability and fusion of the joint surfaces. Customary symptoms include pain and swelling of the joints together with increasing stiffness and disability as the condition continues. The joints may eventually become distorted or deformed.

Another form of arthritis is osteoarthritis which is a degeneration of articular cartilage and bone, a degenerative condition.

For both forms of arthritis conventional therapy has included the use of corticosteroids, initially at a small dose and continued, often increased slowly, for a period of several years until the desired degree of control/mobility is attained. Prednisone is often used. For osteoarthritis an intra-articular injection of corticosteroids is often recommended for acute inflammations and episodes. Other treatments have included the administration of salicylates, notably aspirin, gold salts, ibuprofen, indomethacin, oxyphenbutazone and the like.

Among the advantages of the method of the present invention the patient is able to consume the required amount of bisulfite orally and without the danger of seroid therapy and its attendant risks, or the stomach upset and blood anormalities often associated with other products, such as indomethacin. The bisulfite itself is a safe, food-grade product well tolerated by virtually all patients.

In some of the clinical studies reported below there has been a complete remission of symptoms and therapy is stopped; in other patients therapy is maintained for longer periods of time and probably may be continued indefinitely.

In one aspect, use of the present invention leads to symptomatic and objective improvement in arthritic symptoms and conditions in man. By the term "symptomatic improvement", as used herein, reference is had to an improvement in subjective symptoms as reported by that patient. By the term "objective improvement", as used herein, reference is had to a measurable and objective change in the patient's condition.

Other and further aspects, objects, purposes, advantages, aims, utilities, features and the like will be apparent to those skilled in the art from a reading of the present application.

DETAILED DESCRIPTION OF THE INVENTION

More particularly, this invention concerns a process for treating a human suffering from the symptoms of arthritis wherein there is introduced preferably orally into such a human a pharmaceutically effective amount of sodium bisulfite.

In one preferred mode of using this invention, an aqueous solution of from about 1 to 15% by weight sodium bisulfite is prepared. Such solution is orally consumed by a human at the total (or accumulated) dose rate ranging from 0.2 to 4.0 mg per each kilogram of body weight per day, more preferably in the form of from two to four spaced doses per day, each such dose being preferably taken after meal time. A presently most preferred dose rate comprises one in the range from about 1.0 to 3.4 mg per kg. of body weight per day taken in the form of at least two spaced oral doses (using an aqueous solution as described herein).

In such mode of using this invention, one achieves symptomatic improvement in arthritic symptoms.

It is believed that larger or smaller doses may be used in accordance with the spirit and scope of the present invention. One dose rate, for example, considered effective is in the range of about 0.2 to 150 mg per day for an average human adult patient of approximately 70 kg. One knowledgeable in this art will select a regimen of therapy that provides subjective, symptomatic relief to the patient. Dose ranging studies in human volunteers indicate that single doses of up to 1,000 mg of sodium metabisulfite are tolerated without adverse effects.

The use of this invention is preferably practiced at present using a dilute aqueous solution of sodium bisulfite. Because of the tendency for sodium bisulfite to undergo oxidation when in aqueous solution and oxygen is present, it is presently common and even preferred in using this invention to employ a solution which comprises on a 100 percent by weight total solution basis:

(a) from about 1 to 15 percent by weight of dissolved inorganic solids, and
(b) the balance up to 100 percent by weight of any given solution being water.

In such solution, such dissolved inorganic solids comprise on a calculated 100 percent by weight dry basis:

(a) at least about 50 and more preferably at least 90 percent by weight sodium bisulfite, and
(b) the balance up to 100 percent by weight thereof being inorganic compounds produced or producible by the oxidation of sodium bisulfite.

The water used in such a solution is preferably purified (e.g. filtered, deionized, distilled or the like). After preparation, such a solution is preferably stored in a closed container to reduce oxidation.

Such an aqueous solution can be directly consumed by a patient as drops (e.g. from about 5 to 20 drops per meal, depending upon dose rate for an individual patient) or as a capsule or the like, as desired. Individual dosage units can range from about 50 to about 500 mg. each.

Symptomatic improvement in a patient's condition may occur within a few days to a few weeks of continuous usage of sodium bisulfite in accord with the teachings of this invention and as illustrated below.

One important advantage of the present invention is the circumstance that the indicated desirable results are achieved with surprisingly little or no apparent side effects.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF THE SOLUTION

A sodium bisulfite is prepared by dissolving pharmaceutical grade (U.S.P. Grade) powdered sodium bisulfite (sodium metabisulfite) in distilled water at room temperature to form an eleven percent by weight aqueous solution.

This solution is then placed into a series of plastic squeeze bottles, each with a volumetric capacity of about 50–52 ml. Each bottle is provided with a cap permitting drop-wise dispensing of solution from such bottle at an estimated rate of 13 drops per ml. This is sometimes identified below as Agent C. In the studies reported below no other form of anti-arthritic therapy was used unless otherwise indicated.

In each of the following numbered case histories, each patient is provided with such a bottle of the above solution and is instructed to dose himself (or herself, as the case may be) from the bottle so provided at the rate indicated (in drops) to be taken orally at the frequency stated, preferably after each of his (her) three daily meals. When the contents of one such bottle is thus so gradually consumed by an individual patient, another is provided to him (her).

EXAMPLE 1

A 28 year old woman, 55 kilograms body weight, temperature 37° C., blood pressure 120/70 was examined. Rheumatoid arthritis was diagnosed based on clinical study and immunological tests.

The patient's symptoms consisted of pains in the interfalangical articulations, both hands, as well as a discrete deformation on one hand. Previous treatment consisted of antirheumatics and Artilan suppositories, used normally in severe phases of this illness. At first there was a discrete improvement, followed by pain which increased in intensity using this conventional therapy. Sodium bisulfite solution 11%, as described above, was prescribed 10 drops per dose, twice daily. Approximately 10 days later there was a favorable improvement, pain disappeared and up to the present this patient continues with this same treatment with a 10 drops dose twice a day; the deformity has not progressed and patient is comfortable.

EXAMPLE 2

A woman, 38 years old, 70 kilograms body weight, 37° C., blood pressure 140–90 was diagnosed as having rheumatoid arthritis based on specific tests including the Rheumatoid factor and others. The pathological state started approximately four months prior to treatment with pain in the articulations of both hands; no deformity was observed. Intensity of the pain was of a moderate degree. This patient had also received an antirheumatic treatment. Previous therapy was stopped and the patient was given a solution of sodium metabisulfite, as described above, to be taken at a rate of one drop per every ten kilograms of body weight, i.e. 7 drops, three times a day.

The desired effect appeared approximately ten days after therapy with sodium metabisulfite was initiated. This patient reported having experienced some disagreeable slight manifestations, so the dose was diminished to 5 drops 3 times a day, and those slight manifestations disappeared as well as the pain in the articulations. This patient continues to be maintained with the prescribed dose.

EXAMPLE 3

A 58 year old man, 75 kilograms body weight, temperature 37° C., blood pressure 150/90. This patient began deforming rheumatoid arthritis approximately 20 years ago. The intense deformation was localized in both hands, accompanied with severe pains. Prednisone, analgesics and anti-inflamatories were prescribed unsuccessfully.

A 11% aqueous sodium metabisulfite solution was prescribed for the patient, 7 drops 3 times daily, and after 30 days therapy all the pains disappeared. This patient was followed for 2 years and continues to be free of pain; the joint deformation has not continued.

EXAMPLE 4

A 52 year old woman, 65 kilograms body weight, temperature 37° C., blood pressure 150/85 was diagnosed as having rheumatoid arthritis existing for approximately 7 years. She was treated by various doctors and the diagnosis was made with specific studies.

For a two month period of time this patient was given only Agent C, 6 drops 3 times daily. In only 8 days following initiation of therapy with the sodium bisulfite solution the patient was examined and the inflammation and pains in both hands diminished completely.

EXAMPLE 5

A 22 year old woman, 50 kilograms body weight, temperature 37° C., blood pressure 120/60 was examined and diagnosed as having rheumatoid arthritis (Juvenile). The patient was treated with gold salts and antirheumatics, with no favorable result.

This patient was given Agent C at a rate of 5 drops 3 times daily and observed after a period of approximately 3 months. The analgesic and anti-inflammatory effects of Agent C were very noticeable, the intensity has diminished considerably, as well as the inflammation. Therapy continues at the same rate.

EXAMPLE 6

A woman, age 76, 53 kg. weight, blood pressure 120/90, temperature 35.8°–36.2° C. was diagnosed as having arthritis as evidenced by deformation in the toes and fingers. Agent C was employed at a rate of 6 drops twice daily. Twenty days following initiation of therapy the patient reported that pains were diminished, and the patient appeared to be in better health. After about 4 months of therapy pains had disappeared completely; inflammation was still present but to a smaller degree.

This patient was followed for one year, maintained at the same dosage level of Agent C and continued to be free from pain with relatively no inflammation.

EXAMPLE 7

A woman, age 78, weight 56 kg., temperature 36.4° C., blood pressure 122/80, was examined and diagnosed as having arthritis. Symptoms included inflammation of the finger joints progressing over a 20 year period, with eventual difficulty in grasping objects in her hands. Therapy was initiated with Agent C, 5 drops 3 times a day. After approximately 15 days, pain in the finger joints subjectively ceased. Finger deformation was still present, even after extended period of therapy, although the fingers did not appear to have increased in size.

EXAMPLE 8

A woman, age 46, 68 kg., was diagnosed as having arthritis. Agent C was administered 7 drops twice daily and the patient observed. After one year's therapy the patient complained of no pains and inflammation was virtually completely gone.

What is claimed is:

1. A method of treating arthritis and arthritic conditions in a person suffering from the symptoms of arthritis comprising orally administering to said person a symptom-alleviating amount of a compound selected from the group consisting of alkali metal sulfites and alkali metal bisulfites at an effective rate of from about 0.2 to about 50 mg. thereof per kilogram of body weight per 24 hours.

2. The method of claim 1 in which the compound is sodium bisulfite.

3. The method of claim 1 in which the compound is sodium metabisulfite.

4. The method of claim 1 in which the person is suffering from rheumatoid arthritis.

* * * * *